United States Patent
Lee et al.

(10) Patent No.: US 6,886,939 B2
(45) Date of Patent: May 3, 2005

(54) TOPOGRAPHER AND METHOD FOR MAPPING CORNEAL SURFACE

(75) Inventors: Kyu Haeng Lee, Kyonggi-do (KR); Han Chul Lee, Incheon (KR); Hyuk Je Kwon, Kyonggi-do (KR)

(73) Assignee: Huvitz Co., Ltd., Kyonggi-Do (KR)

( * ) Notice: Subject to any disclaimer, the term of this patent is extended or adjusted under 35 U.S.C. 154(b) by 236 days.

(21) Appl. No.: 10/265,138

(22) Filed: Oct. 7, 2002

(65) Prior Publication Data
US 2003/0231284 A1 Dec. 18, 2003

(30) Foreign Application Priority Data
Jun. 18, 2002 (KR) ........................................ 2002-33892

(51) Int. Cl.[7] ................................................. A61B 3/10
(52) U.S. Cl. ...................................................... 351/212
(58) Field of Search ................................. 351/205, 212, 351/219, 221, 246, 247; 606/4, 5, 16

(56) References Cited

U.S. PATENT DOCUMENTS 5,521,657 A * 5/1996 Klopotek .................... 351/212

* cited by examiner

Primary Examiner—George Manuel
(74) Attorney, Agent, or Firm—Staas & Halsey LLP

(57) ABSTRACT

A topographer for mapping the central portion as well as the peripheral portion of the corneal surface is disclosed. The topographer includes a chart image generating part for producing a chart image to fixate the gaze of an eye under test; a measuring light source for projecting concentric ring-shaped measuring lights to the cornea of the eye; a light detector for detecting the image of the measuring light reflected from the cornea; and a vertex measuring optical system. The vertex measuring optical system comprises a vertex measuring light source for radiating a vertex measuring light; a vertex beam splitter for separating the vertex measuring light into two beams; a vertex measuring light projector for projecting one of the two beams to the corneal vertex of the eye, and capable of moving along the surface of the corneal vertex; a collimator for projecting the other beam to a scanning mirror; and a vertex measuring light detector for detecting a light signal produced by superimposing and interfering the two beams reflected from the scanning mirror and the corneal vertex.

11 Claims, 5 Drawing Sheets

TOPOGRAPHER AND METHOD FOR MAPPING CORNEAL SURFACE

FIELD OF THE INVENTION

The present invention relates to a topographer and a method for mapping the corneal surface of an eye, and more particularly, to a topographer for mapping the central portion as well as the peripheral portion of the corneal surface, and optionally for measuring the refractive power of an eye under test.

BACKGROUNDS OF THE INVENTION

The apparatus for measuring the shape of corneal surface is an ophthalmic apparatus which is useful for prescribing contact lens or for examining the corneal shape before and after an LASIK(Laser Associated Stromal In situ Keratomileusis) operation. The apparatus for measuring the shape of the corneal surface is generally called as a corneal topographer. Recently developed corneal topographer can also obtain the thickness of the cornea by measuring the shape of the endothelial surface and the shape of the epithelial surface thereof.

A prior topographer radiates an LED light of an infrared wavelength onto a cornea from a single ring shaped light source, detects the ring image reflected from the cornea with a two-dimensional CCD (Charge Coupled Device), and obtains the curvature of the cornea by analyzing the reflected ring image. In an improved topographer, the light source is designed to include a plurality of illumination rings, and thereby one can obtain the two-dimensional curvature distribution of the cornea by analyzing the ring images reflected from the cornea. Meanwhile, a multi-functional ophthalmic apparatus for measuring the shape of the corneal surface and the refractive power of an eye at the same time is also developed.

FIG. 1 is a drawing to illustrate the optical system of the conventional corneal topographer. As shown in FIG. 1, the conventional corneal topographer comprises a chart image generating part 20 for projecting an image to fixate the gaze of the examined eye 1; a collimating light source 30 for projecting a collimating light to fixate the position of the eye 1 with respect to the topographer; a measuring light source 32 for projecting concentric ring-shaped measuring lights to the cornea 2 of the eye 1; and a light detector 40 for detecting the images of the collimating light and the measuring lights reflected from the cornea 2 of the eye 1. The chart image generating part 20 comprises a lamp 22 for radiating a visible light; and a chart 24 for passing the light produced by the lamp 22, and generating a chart image to be projected to the eye 1.

In operation, the visible light radiated from the lamp 22 of the chart image generating part 20 passes through the chart 24, and forms a chart image. The image formed at the chart 24 is projected to the retina 3 of the eye 1 through the first relay lens 25, a reflecting mirror 26, the second and third relay lens 27,28, the first and the second beam splitter mirror 35,36, and the cornea 2. The patient fixates his or her gaze at the produced chart image, which prevents the measurement error of the corneal shape due to the movement of the eye 1 to be examined.

When the gaze of the eye 1 is fixated, the collimating light is radiated from the collimating light source 30. The collimating light passes through an objective lens 34 and the first beam splitter mirror 35 and forms an image of the collimating light at the cornea 2. The image of the collimating light reflected from the cornea 2 is partially reflected by the first beam splitter mirror 35, and then the partially reflected image passes through the third relay lens 28, the second beam splitter mirror 36 and the fourth relay lens 37, and forms the reflected image of the collimating light on the light detector 40. The operator moves the position of the topographer to most clearly detect the image of the collimating light formed with the light detector 40, so that the position of the eye to be examined is properly fixated with respect to the topographer.

When the gaze and the position of the eye 1 are fixated, a plurality of the concentric ring-shaped measuring lights is radiated to the cornea 2 of the eye 1 from the measuring light source 32. The measuring lights reflected from the cornea 2 pass through the first beam splitter mirror 35, the third relay lens 28, the second beam splitter mirror 36, and the fourth relay lens 37, and form the ring-shaped images of the measuring lights reflected by the cornea 2 on the light detector 40. The shapes of the measuring light images formed on the light detector 40 changes according to the corneal shape of the eye 1. Thus, the shape of the corneal surface and the curvature of the cornea can be calculated and obtained by analyzing the images formed on the light detector 40 with a conventional processor installed in the topographer. In summary, the conventional topographer radiates ring images from the measuring light source 32 consisting of LEDs of the Placido ring type to the cornea 2 of the eye 1, and the light detector 40 of the topographer detects the ring images reflected from the cornea 2. Then the topographer calculates the shape and the curvature of the corneal epithelial surface by analyzing the size and the shape of the reflected ring images. In order to measure the thickness of the cornea 2 with a conventional topographer, a slit-shaped light is additionally projected from a light source (Not shown) to the cornea 2 with a slanting angle, and a detector (Not shown) detects the slit-shaped light reflected at the endothelial surface of the cornea 2 to obtain the shape of the endothelial surface of the cornea 2. The thickness of the cornea 2 can be obtained from the information relating the shapes of epithelial surface and the shape of the endothelial surface of the cornea 2.

However, in the conventional topographer, it is structurally impossible to obtain the ring images reflected at the vertex of cornea 2. Namely, the ring images from the measuring light source 32 are reflected only at the peripheral portion of the cornea 2 rather than the central portion thereof. Therefore, the shape and the thickness of the corneal vertex portion (i.e., the central portion) having a convex shape of a diameter of about 1 mm cannot be measured with the conventional topographer. Due to this restriction, the operation on cornea, such as the LASIK operation is performed without accurate information on the shape and thickness of the central portion of the cornea 2. In addition, the conventional topographer consists of only various lenses and mirrors. Thus, the topographer should be assembled very precisely, and the accuracy of the measurement is deteriorated as the topographer is used.

FIG. 2 is a drawing for illustrating the optical system of the conventional refractometer having an additional function of measuring a corneal curvature. As shown in FIG. 2, the conventional refractometer comprises a chart image generating part 20 for fixating the gaze of the examined eye 1 and performing a fogging process to blur a focus of the eye 1; a measuring light source 10 for projecting a measuring light to the retina 3 of the eye 1 for measuring a refractive power of eye 1; a measuring light detecting part 12 for receiving the measuring light reflected from the retina 3 of the eye 1; and a light detector 40 for detecting the chart image reflected from the retina 3 of the eye 1 in order to perform the fogging process. The refractometer shown in FIG. 2 further includes mire ring 5 for radiating a ring-shaped measuring light to measure the corneal curvature.

In operation, a visible light produced by the lamp 22 of the chart image generating part 20 passes through the chart 24. The chart image formed at the chart 24 is projected to form the chart image on the retina 3 of the eye 1 through the first relay lens 25, a reflecting mirror 26, the second and the third relay lens 27,28, and the first and the second beam splitter mirror 35, 36. Meanwhile, an image of the eye 1 produced by an illuminating light (not shown) is projected to the light detector 40 through the first and the second beam splitter mirror 35, 36, the third relay lens 28, and the fourth relay lens 37. The operator aligns the optical axis of the ophthalmic apparatus and eye 1 by detecting the image of the eye 1 formed on the light detector 40. Then the "fogging operation" is carried out to relax the eye 1 to be examined. In detail, the operator adjusts the position of the first relay lens 25 so that the eye 1 is focused to the chart image. Then the first relay lens 25 is controlled to move a position at which the eye 1 cannot be focused to the chart image. This process makes the intraocular lens of the eye 1 to be relaxed, and the refractive power is measured under this relaxing condition After completing the fogging operation, the refractive power measuring light is projected from a measuring light source 10. The measuring light radiated from a measuring light source 10 is condensed by the fifth relay lens 11, passes through the center of a hole mirror 19, and projected to the retina 3 of the eye 1 through an objective lens 34 and the first beam splitter mirror 35. The measuring light reflected from the retina 3 passes through the first beam splitter mirror 35, is reflected by a hole mirror 19, is separated by a six-holes plate 13 into six measuring lights. The six measuring lights are condensed by the sixth relay lens 14, and projected to a light detector 15. The propagation directions of the six measuring lights separated by the six-holes plate 13 are changed according to the refractive power of the eye 1 to be examined. Thus, the refractive power of the eye 1 can be calculated by analyzing the images of the six measuring lights formed on the light detector 15.

In measuring the corneal curvature with the ophthalmic apparatus shown in FIG. 2, a ring-shaped light is projected to the cornea 2 of the eye 1 from a mire ring 5. The ring-shaped light reflected from the cornea 2 of the eye 1 passes through the first and the second beam splitter mirrors 35,36 and is projected to the light detector 40. The corneal curvature can be measured from the degree of the distortion of the ring-shaped light projected to the light detector 40.

In the above described conventional ophthalmic apparatus, all of the optical components are fixed to an optical base, and the signal reflected from the retina 2 overlaps with the signal reflected from the surface of the optical components disposed between the light detector 15 and the retina 2, which may produce data-distortions. If a light radiated from a light source is projected to the eye with a predetermined angle with respect to an optical axis of the eye to be examined, such distortion can be avoided. However, such ophthalmic apparatus is very complex in its configuration, and should be controlled very precisely. In addition, the images of the six measuring lights formed on the light detector 15 are significantly varied in their sizes according to the refractive power of the eye 1, which may increase the measurement error.

SUMMARY OF THE INVENTION

Accordingly, it is an object of the present invention to provide a corneal topographer capable of accurately measuring the shape and thickness of the central portion as well as the peripheral portion of a corneal surface.

It is other object of the present invention to provide a corneal topographer which has improved measurement accuracy and prolonged lifetime by manufacturing some parts of optical system with optical fibers.

It is another object of the present invention to provide the corneal topographer capable of measuring refractive power with reduced measurement error.

In order to achieve these objects, the present invention provides a topographer for measuring the shape of a corneal surface comprising a chart image generating part for producing a chart image to fixate the gaze of an eye under test; a measuring light source for projecting concentric ring-shaped measuring lights to the cornea of the eye; a light detector for detecting the image of the measuring light reflected from the cornea; and a vertex measuring optical system. The vertex measuring optical system comprises a vertex measuring light source for radiating a vertex measuring light; a vertex beam splitter for separating the vertex measuring light into two beams; a vertex measuring light projector for projecting one of the two beams to the corneal vertex of the eye, and capable of moving along the surface of the corneal vertex; a collimator for projecting the other beam to a scanning mirror; and a vertex measuring light detector for detecting a light signal produced by superimposing and interfering the two beams reflected from the scanning mirror and the corneal vertex.

The present invention also provides a method for measuring the shape of the corneal surface with a topographer comprising the steps of: fixating the gaze of an eye to be examined by projecting a chart image to the eye; fixating the position of the eye with respect to the topographer; and projecting concentric ring-shaped measuring lights to the cornea of the eye and measuring the shape of the peripheral portion of the corneal surface by detecting the concentric ring-shaped measuring lights reflected by the cornea. The method further includes the steps of separating a vertex measuring light into two beams, projecting one of the two beams to the corneal vertex of the eye, and projecting the other beam to a scanning mirror. The two beams reflected from the scanning mirror and the corneal vertex are superimposed and interfered, and the shape of the corneal vertex is measured from the interference intensity of the two beams.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein

FIG. 5 shows a plan view and a cross sectional view of a micro-lens array for condensing and refracting light, which

DETAILED DESCRIPTION OF THE INVENTION

Figure 1:
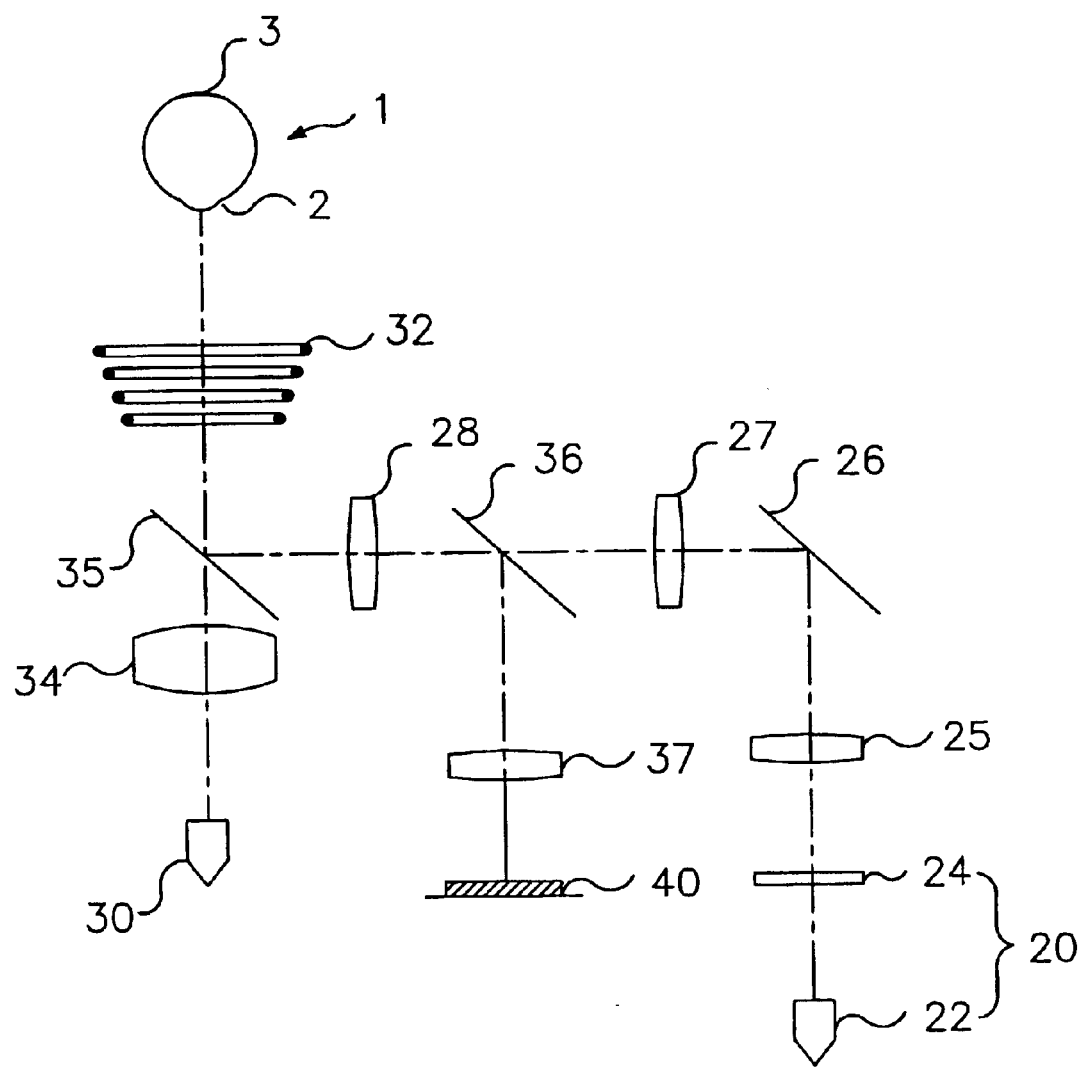
FIG. 1 is a drawing for illustrating the optical system of a conventional corneal topographer.
Figure 2:
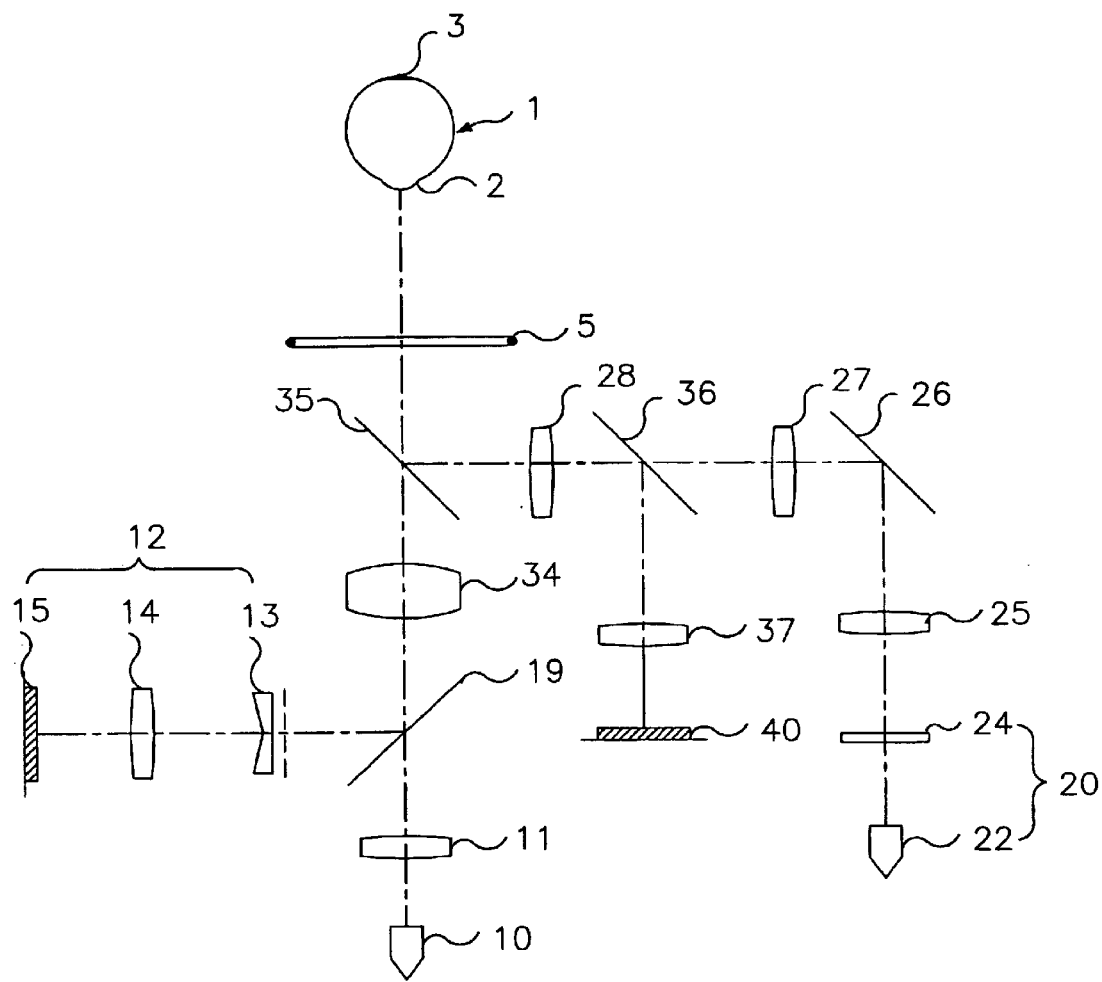
FIG. 2 is a drawing for illustrating the optical system of a conventional refractometer having an additional function of measuring a radius of a corneal curvature.

Hereinafter, the preferred embodiments of the present invention will be described with reference to the attached drawings. In the following description and drawings, the same reference numerals are provided to elements performing the same functions.

Figure 3:
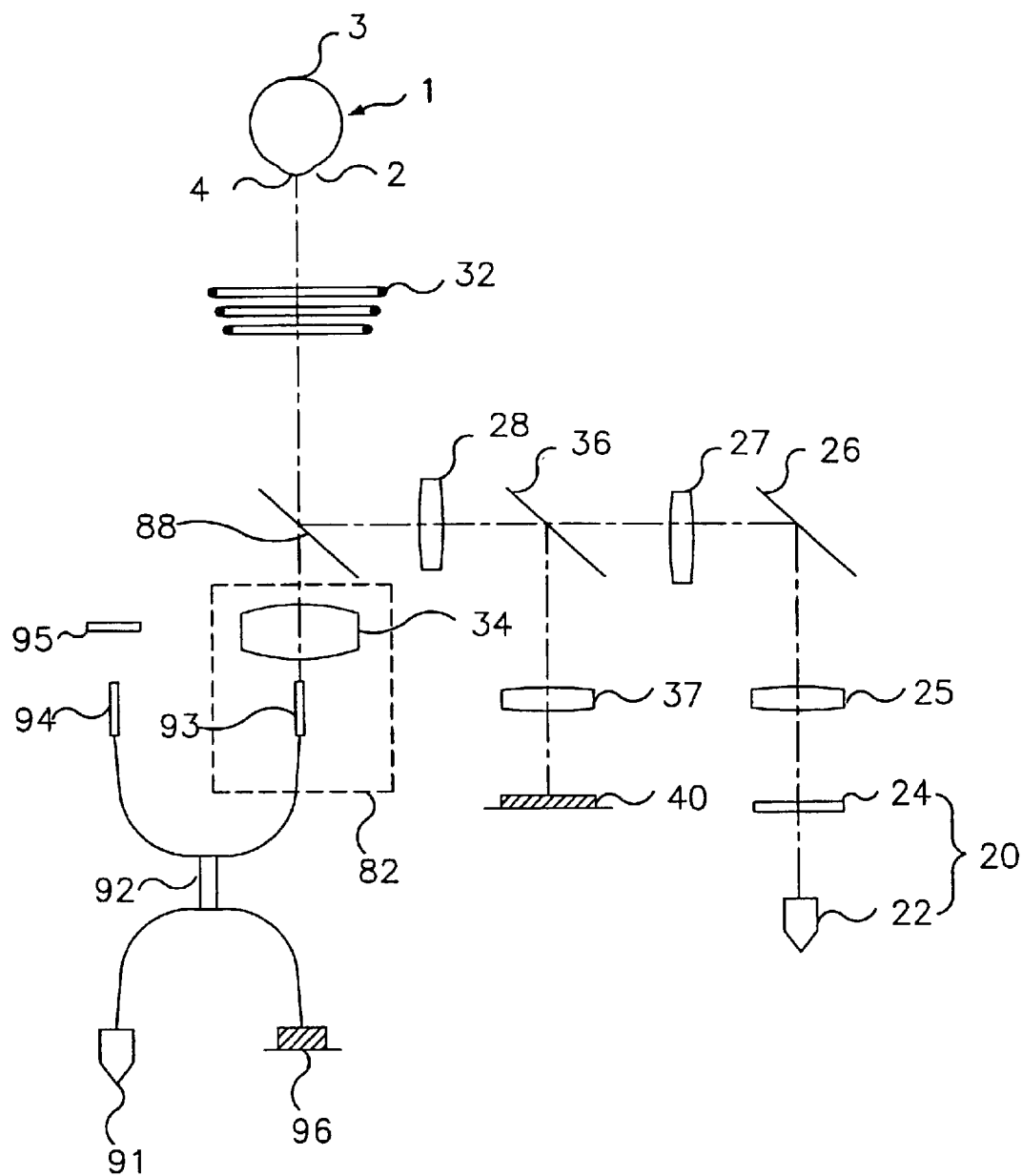
FIG. 3 is a drawing for illustrating the optical system of a corneal topographer according to an embodiment of the present invention.

FIG. 3 is a drawing for illustrating the optical system of a corneal topographer for measuring the shape of corneal surface according to an embodiment of the present invention. As shown in FIG. 3, the topographer according to an embodiment of the present invention comprises a chart image generating part 20 for producing a chart image for fixating the gaze of the eye 1 to be examined; a measuring light source 32 for projecting concentric ring-shaped measuring lights to the cornea 2 of the eye 1, and a light detector 40 for detecting the image of the measuring light reflected from the cornea 2. The chart image generating part 20 comprises a lamp 22 for radiating a visible light, and a chart 24 for passing the visible light produced by the lamp 22 and generating a chart image to be projected to the eye 1. As the measuring light source 32, conventional placido ring shaped LED arrays can be used, and a conventional CCD (charge coupled device) can be used as the light detector 40.

In addition, the topographer according to an embodiment of the present invention includes a vertex measuring optical system for measuring the shape and the thickness of the corneal vertex 4, i.e., the central portion of the cornea 2. The vertex measuring optical system includes a vertex measuring light source 91 for radiating a vertex measuring light, a vertex beam splitter 92 for separating the vertex measuring light into two beams; a vertex measuring light projector 93 for projecting one of the two beams to the corneal vertex 4 of the eye 1 and capable of moving vertically or horizontally along the surface of the corneal vertex 4; a collimator 94 for projecting the other beam to a scanning mirror 95; and a vertex measuring light detector 96 for detecting a light signal produced by superimposing and interfering the two beams reflected from the scanning mirror 95 and corneal vertex 4. Preferably, the vertex measuring light source 91, the vertex beam splitter 92, the vertex measuring light projector 93, the collimator 94 and the vertex measuring light detector 96 form a Michelson interferometer, and are connected by optical fibers for transmitting light signals.

Hereinafter, the operation of the topographer according to an embodiment of the present invention will be described. A visible light radiated from the lamp 22 of the chart image generating part 20 passes through the chart 24, and a chart image to be projected to eye 1 is produced at the chart 24. The chart image may have proper patterns for attracting user's attention, for example, can be a geometric image, an animal image, a scenery image, or cartoon image or the like. The chart image is condensed at the first relay lens 25 and reflected by the reflecting mirror 26. The chart image reflected by the reflecting mirror 26 passes through the second and the third relay lens 27,28, is reflected by a hole mirror 88, and then forms the chart image on retina 3 of the eye 1 through the cornea 2. The user fixates his or her gaze to the chart image, which prevents the measurement error of the corneal shape due to the movement of the user's gaze.

When the user's gaze is fixated, the vertex measuring light projector 93 is adjusted to the direction of the vertex 4 of the cornea 2, and the vertex measuring light is radiated from the vertex measuring light source 91. The vertex measuring light is separated into two beams by the vertex beam splitter 92, and one of the two beams is projected to the vertex 4 of the cornea 2 through the vertex measuring light projector 93, objective lens 34 and the hole mirror 88. The image of the vertex measuring light reflected by the cornea 2 is reflected by the hole mirror 88. The image reflected by the hole mirror 88 is condensed at the third relay lens 28, reflected by the beam splitter 36, and condensed by the fourth relay lens 37 to form the image of the vertex measuring light which is formed at the vertex 4 on the light detector 40. The operator moves the position of the topographer with respect to eye 1 to most clearly detect the image formed on cornea 2 so that the position of the eye 1 is most properly fixated with respect to the topographer's optical system.

When the gaze and the position of the eye 1 are determined, the shape of the peripheral portion of the cornea 2 is measured with the measuring light source 32, and the shape of the central portion of the cornea 2 is measured with the vertex measuring light source 91 while moving the vertex measuring light projector 93 along the surface of the corneal vertex 4.

For measuring the shape of the peripheral portion of the cornea 2, the concentric ring-shaped measuring lights is projected from the measuring light source 32 to the cornea 2 of the eye 1, and reflected thereby. The ring-shaped measuring lights reflected by the cornea 2 are reflected by the hole mirror 88, and are condensed by the third relay lens 28. Then the ring-shaped measuring lights is reflected by a beam splitter 36, and is condensed by the fourth relay lens 37 to form the reflected images of the measuring lights on the light detector 40. The shape of the images of the measuring lights formed on the light detector 40 changes according to the shape of the epithelial surface of the cornea 2. Thus, by analyzing the shape of the images formed on the light detector 40 with a conventional processor mounted in the topographer, the shape and/or curvature radius of the peripheral portion of the cornea 2 except the central portion thereof can be obtained.

The vertex measuring optical system for measuring the shape and/or thickness of the vertex 4 of the cornea 2 constitutes Michelson interferometer which is preferably formed with optical fibers. The vertex 4 of the cornea 2 means a central portion of cornea 2 having a diameter of 1–2 mm. For measuring the shape of the central portion of the cornea 2, the vertex measuring light source 91 radiates the vertex measuring light. The radiated vertex measuring light is separated by the vertex beam splitter 92 into two beams. One of the two beams is projected to the cornea 2 through the vertex measuring light projector 93, and the other beam is projected to the scanning mirror 95 through the collimator 94. The beam reflected from the corneal vertex 4 and the beam reflected from the scanning mirror 95 return to the Michelson interferometer, and are superimposed and interfered at the beam splitter 92, and then projected to the vertex measuring light detector 96. The interference intensity of the superimposed beams is used to obtain the shape of the central portion of the cornea 2. That is, the beam reflected from the cornea 2 and the beam reflected from the scanning mirror 95 is superimposed at the beam splitter 94 which works as a 3 dB coupler. The vertex measuring light projector 93 transmits the vertex measuring light for measuring the shapes of the endothelial and epithelial surfaces of the corneal vertex 4, and is fixed on a stage 82. The stage 82 is mounted in the topographer so that it can be moved vertically and horizontally in a step of about 10 to 950 $\mu$m along the surface of the corneal vertex 4. Thus, the shape of the corneal vertex 4 can be measured by analyzing the interference intensity of the superimposed beams while moving the stage 82. The scanning mirror 95 is mounted in the topographer so that it can be moved along the axis of the beam projected thereto from the collimator 94. Thus, the endothelial shape of the corneal vertex 4 can be measured by analyzing the interference intensity of the superimposed beams while moving the scanning mirror 95. In summary, the shape and/or thickness of the vertex 4 of the cornea 2 can be accurately measured by analyzing the interference intensity of the superimposed beams while moving the stage 82 and the scanning mirror 95.

Figure 4:
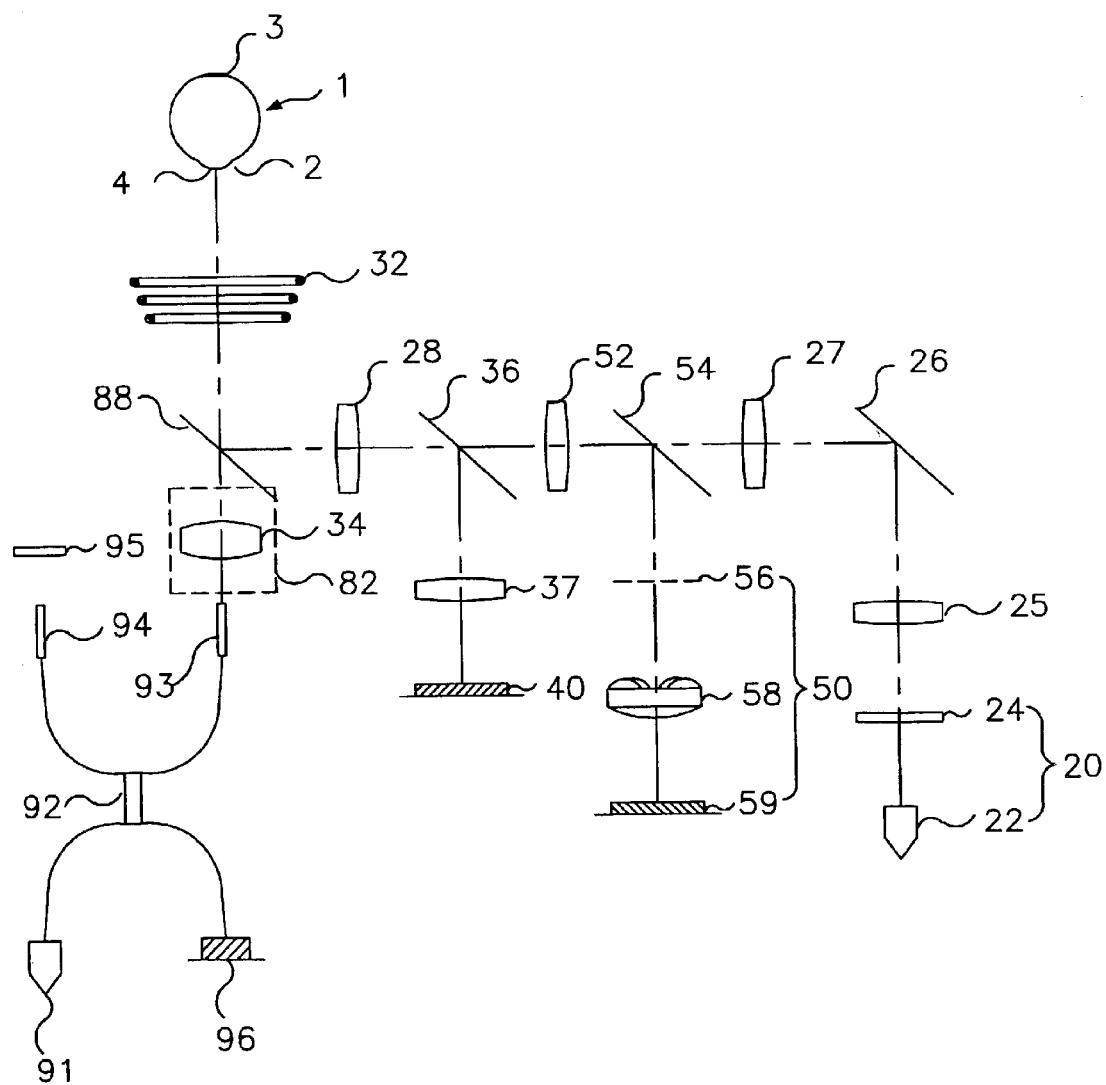
FIG. 4 is a drawing for illustrating the optical system of a corneal topographer according to other embodiment of the present invention.

FIG. 4 is a drawing for illustrating the optical system of a topographer according to other embodiment of the present invention. The topographer shown in FIG. 4 further includes an optical system for measuring the refractive power of an eye compared to the topographer shown in FIG. 3. The optical system for measuring the refractive power utilizes the beam radiated from the vertex measuring light projector 93 as a refractive power measuring light. The light receiving part 50 for detecting the refractive power measuring light includes a hole plate 56 for separating the measuring light reflected from the retina 3 into a plurality of the beams, preferably into six beams, a micro-lens array 58, and the light detector 59. In addition, the fifth relay lens 52 and the beam splitter 54 may be formed, for example, between the beam splitter 36 and the second relay lens 27 for directing refractive power measuring light reflected from the retina 3 to the light receiving part 50. Furthermore, a stage for moving the first relay lens 25 can be mounted in the topographer for temporarily focusing the chart 24 to the examined eye 1 and performing the fogging operation.

In the topographer shown in FIG. 4, the chart focusing and fogging operation are performed with the chart image generating part 20 to measure the refractive power of the eye 1. The visible light emitted from the lamp 22 of the chart image generating part 20 produces the chart image while passing the chart 24. The chart image is condensed by the first relay lens 25, reflected by the reflecting mirror 26, condensed by the second and the third relay lens 27, 28, and reflected again by the hole mirror 88 to form the chart image on the retina 3 of the eye 1. The first relay lens 25 is mounted to move along on the propagation direction of the chart image. Thus, the operator observes the chart image formed on the retina 3 of the eye 1 with the light detector 40, and controls the position of the first relay lens 25 so as to focus the eye 1 to the chart image. When the eye 1 is focused to the chart image, the operator performs the fogging operation by moving the first relay lens 25 so that the eye 1 could not be focused to the chart image. By this fogging operation, the intraocular lens of the eye 1 is relaxed, and the refractive power of the eye 1 is measured under this relaxing condition.

After completing the fogging process, a refractive power measuring light is radiated from the vertex measuring light projector 93 to the retina 3 of the eye 1. The measuring light is reflected at the retina 3, and then is projected to the light receiving part 50 via the hole mirror 88, the third and the fifth relay lens 28, 52, and the beam splitter 54. The refractive power measuring light projected to the light receiving part 50 is separated into six split beams by a six holes plate 56, is condensed and refracted by a micro-lens array 58, and then is projected to the light detector 59. Since the propagation directions of the six split beams projected to the light detector 59 are changed according to the refractive power of the eye 1, the spherical reflective power and/or the cylindrical reflective power of the eye 1 can be calculated from the length of the major axis and the minor axis of the ellipse formed by the six split beams.

Figure 5:
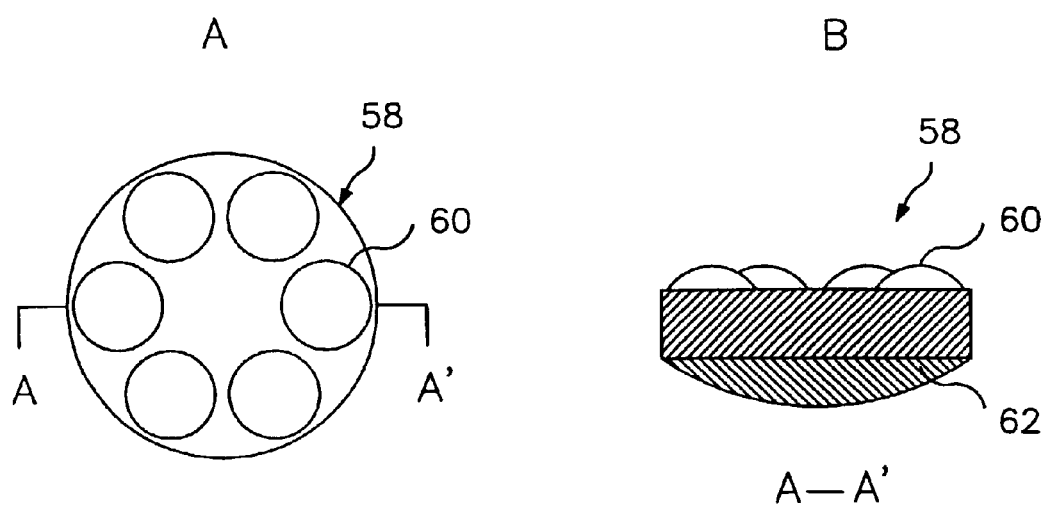

The topographer shown in FIG. 4 includes the micro-lens array 58 to reduce the measurement error due to the variation of the ocular refractive power of the eye 1. The micro-lens array 58 is designed to not only condense but also refract the six split beams. FIG. 5 shows a plan view (A) and a cross sectional view (B) of the micro-lens array 58. As shown in FIG. 5, the micro-lens array 58 includes a plurality of condensing lenses 60 and a refracting lens 62. The plurality of condensing lenses 60 is located on the propagation directions of the six split beams for condensing the six split beams, respectively, and is formed at the front side of the micro-lens array 58. The refracting lens 62 is formed at the back side of the micro-lens array 58 to refract the six split beams condensed by the plurality of condensing lenses 60 to the center of the light detector 59. The number of the condensing lenses 60 is determined according to the number of holes formed on the plate 56, and is determined to include minimum information for calculating the refractive power of the eye 1. By disposing the condensing lenses 60 at the front side and the refracting lens 62 at the back side, the image of the split beams which is sensitively changed according to the refractive power of the eye 1 can be accurately formed on the detector 59. Namely, the micro-lens array 58 condenses and refracts the measuring light reflected at the retina 2 so that the six split beams can be properly focused to the light detector 59, and the distortion of the six split beams due to the refractive power of the eye 1 can be reduced.

In the topographer according to an embodiment of the present invention, the optical system for measuring the shape of the corneal surface and the optical system for measuring the refractive power are arranged in parallel. Namely, the propagation direction of the light projected to the light detector 59 for measuring the refractive power and the propagation direction of the light projected to the light detector 40 for measuring the shape of the peripheral portion of the corneal surface are perpendicular to the main direction of the light propagations at which the reflecting mirror 26 and the beam splitter 36 are disposed. By arranging the reflective optical system and the optical system for measuring the shape of the corneal surface in parallel, the measurement error can be minimized.

Hereinafter, a method for continuously measuring the ocular refractive power and the shape of the corneal surface of an eye with the corneal topographer shown in FIG. 4 will be described. However, it should be noted that the ocular refractive power and the shape of the corneal surface could be measured separately and the measuring order could be also changed.

In order to continuously measure the ocular refractive power and the shape of the corneal surface, the measuring light source 32 or a separate illuminating light (Not shown) equipped at the front of the topographer is turned on. Then, the position of the topographer head is adjusted to properly fix the optical axis of the eye with respect to the optical system of the topographer. The lamp 22 is turned on, and the first relay lens 25 is moved so that the eye 1 is focused to the chart image formed by the chart 24. After the eye 1 is focused to the chart image, the position of the first relay lens 25 is fixed, and the pseudo refractive power of the eye 1 is measured. With reference to the obtained pseudo refractive power of the eye 1, the first relay lens 25 is moved to perform the fogging operation so that the eye 1 cannot be focused to the chart image. After this fogging operation, the exact refractive power of the eye 1 is measured.

After the exact refractive power is measured, the image of the measuring light source 32 reflected at the cornea 2 is obtained with the light detector 40, and the shape of the peripheral portion of the corneal surface is measured thereby. The measured shape of the peripheral portion of the corneal surface and the reflective power are displayed on a screen (Not shown) of the topographer.

As a next step, the epithelial and the endothelial shapes of the central portion of the corneal surface are measured while moving the vertex measuring light projector 93 and the scanning mirror 95 which are formed at the ends of the Michelson interferometer. With the data obtained from the Michelson interferometer while moving the scanning mirror 95, the internal or the endothelial shape of the central potion of the cornea 2 can be measured. With the data obtained from the Michelson interferometer while moving the vertex measuring light projector 93, the surface or the epithelial shape of the central potion of the cornea 2 can be measured. The intensities of the interference signal of Michelson interferometer obtained at the endothelial and the epithelial surfaces of the corneal vertex 4 are measured with the light detector 96, and a three-dimensional image of the corneal vertex can be obtained by arranging the intensity value corresponding to each position of measurement.

In this disclosure, there is shown and described only the preferred embodiments of the present invention, but, as aforementioned, it is to be understood that the present invention is capable of use in various other combinations and environments and is capable of changes or modifications within the scope of the inventive concepts as expressed herein.

What is claimed is:

1. A topographer for measuring the shape of a corneal surface comprising:

a chart image generating part for producing a chart image to fixate the gaze of an eye under test;

a measuring light source for projecting concentric ring-shaped measuring lights to the cornea of the eye;

a light detector for detecting the image of the measuring light reflected from the cornea;

and a vertex measuring optical system, wherein the vertex measuring optical system comprises a vertex measuring light source for radiating a vertex measuring light; a vertex beam splitter for separating the vertex measuring light into two beams; a vertex measuring light projector for projecting one of the two beams to the corneal vertex of the eye, and capable of moving along the surface of the corneal vertex; a collimator for projecting the other beam to a scanning mirror; and a vertex measuring light detector for detecting a light signal produced by superimposing and interfering the two beams reflected from the scanning mirror and the corneal vertex.

2. The topographer for measuring the shape of a corneal surface according to claim 1, wherein the vertex measuring light source, the vertex beam splitter, the vertex measuring light projector, the collimator and the vertex measuring light detector are connected by optical fibers for transmitting light signals.

3. The topographer for measuring the shape of a corneal surface according to claim 1, wherein the chart image generating part comprises a lamp for radiating a visible light, and a chart for passing the visible light produced by the lamp and generating a chart image to be projected to the eye.

4. The topographer for measuring the shape of a corneal surface according to claim 1, wherein the measuring light source is placido ring shaped LED arrays.

5. The topographer for measuring the shape of a corneal surface according to claim 1, further comprising a light receiving part for detecting a refractive power measuring light radiated from the vertex measuring light projector, wherein the light receiving part includes a hole plate for separating the measuring light reflected from the retina of the eye into a plurality of the beams; and a light detector for detecting the separated plurality of the beams.

6. The topographer for measuring the shape of a corneal surface according to claim 5, further comprising a micro-lens array for is condensing and refracting the six split beams between the hole plate and the light detector.

7. The topographer for measuring the shape of a corneal surface according to claim 6, wherein the micro-lens array includes a plurality of condensing lenses and a refracting lens, and the plurality of condensing lenses is located on the propagation directions of the six split beams for respectively condensing the six split beams, and is formed at the front side of the micro-lens array, and the refracting lens is formed at the back side of the micro-lens array to refract the six split beams condensed by the plurality of condensing lenses to the center of the light detector.

8. The topographer for measuring the shape of a corneal surface according to claim 5, wherein the hole plate separates the measuring light reflected from the retina into six beams.

9. The topographer for measuring the shape of a corneal surface according to claim 5, wherein the propagation direction of the light projected to the light detector for measuring the refractive power and the propagation direction of the light projected to the light detector for measuring the shape of the peripheral portion of the corneal surface are perpendicular to the main direction of the light propagations.

10. A method for measuring the shape of a corneal surface of an eye with a topographer comprising the steps of:

fixating the gaze of the eye by projecting a chart image to the eye;

fixating the position of the eye with respect to the topographer;

projecting concentric ring-shaped measuring lights to the cornea of the eye and measuring the shape of the peripheral portion of the corneal surface by detecting the concentric ring-shaped measuring lights reflected by the cornea;

radiating a vertex measuring light, and separating the vertex measuring light into two beams, projecting one of the two beams to the corneal vertex of the eye, and projecting the other beam to a scanning mirror; and measuring the shape of the central portion of the corneal surface with the interference intensity of the two beams reflected from the scanning mirror and the corneal vertex.

11. The method for measuring the shape of a corneal surface of an eye with a topographer according to claim 10, wherein the step of measuring the shape of the central portion of the corneal surface is carried out while moving the beam projected to the corneal vertex along the surface of the corneal vertex and moving the scanning mirror along the propagation direction of the other beam projected to the scanning mirror.

* * * * *